United States Patent
Benseghir et al.

(10) Patent No.: US 12,310,770 B2
(45) Date of Patent: May 27, 2025

(54) METHOD AND SYSTEMS FOR MOTION-STABILIZED CLINICAL TOOL TRACKING AND VISUALIZATION

(71) Applicant: GE Precision Healthcare LLC, Milwaukee, WI (US)

(72) Inventors: Thomas Benseghir, Yvelines (FR); Yves Trousset, Palaiseau (FR); Raphael Doustaly, Rhône (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 740 days.

(21) Appl. No.: 17/447,684

(22) Filed: Sep. 14, 2021

(65) Prior Publication Data
US 2023/0083936 A1    Mar. 16, 2023

(51) Int. Cl.
| | |
|---|---|
| A61B 6/12 | (2006.01) |
| A61B 6/00 | (2024.01) |
| A61B 6/46 | (2024.01) |
| G06T 7/10 | (2017.01) |
| G06T 7/30 | (2017.01) |

(52) U.S. Cl.
CPC .............. *A61B 6/12* (2013.01); *A61B 6/466* (2013.01); *A61B 6/487* (2013.01); *A61B 6/5264* (2013.01); *G06T 7/10* (2017.01); *G06T 7/30* (2017.01); *G06T 2207/10121* (2013.01); *G06T 2207/30096* (2013.01)

(58) Field of Classification Search
CPC .......... A61B 6/487; A61B 6/5264; A61B 6/12
See application file for complete search history.

(56) References Cited

U.S. PATENT DOCUMENTS

| | | |
|---|---|---|
| 9,142,015 B2 | 9/2015 | Cathier et al. |
| 2010/0161023 A1 | 6/2010 | Cohen et al. |
| 2020/0410666 A1* | 12/2020 | Wagner .................... G06N 3/08 |

OTHER PUBLICATIONS

Hohenforst-Schmidt, W. et al., "Enhancement of Aerosol Cisplatin Chemotherapy with Gene Therapy Expressing ABC10 protein in Respiratory System," Journal of Cancer, vol. 5, No. 5, Mar. 24, 2014, 7 pages.

(Continued)

*Primary Examiner* — Colin T. Sakamoto
(74) *Attorney, Agent, or Firm* — McCoy Russell LLP

(57) ABSTRACT

Various methods and systems are provided for x-ray imaging. In one embodiment, a method includes acquiring a plurality of fluoroscopic images depicting an interventional tool positioned relative to an anatomy of interest of a patient, segmenting the interventional tool in the plurality of fluoroscopic images, measuring motion of the patient in the plurality of fluoroscopic images, correcting the plurality of fluoroscopic images to remove the motion of the patient, registering the segmented interventional tool to the anatomy of interest in the corrected plurality of fluoroscopic images, and displaying images with the segmented interventional tool registered to the anatomy of interest. In this way, a practitioner may view the position and movement of an interventional tool located within a patient relative to static images of the anatomy without motion artifacts or errors induced by patient motion such as respiratory motion or cardiac motion.

20 Claims, 7 Drawing Sheets

(56) References Cited

OTHER PUBLICATIONS

Park, S. et al., "Factors associated with the diagnostic yield of computed tomography-guided transbronchial lunch biopsy," Thoracic Cancer, vol. 8, No. 3, May 2017, 6 pages.

Sachidananda, S. et al., "Electromagnetic Navigational Bronchoscopy (ENB) With Cone Beam Computerized Tomography (CBCT) Guidance—Enablig Surgeons To Overcome Limitations," 16 Ismics Annual Scientific Meeting, Jun. 2016, 1 page.

De Ruiter, Q. et al., "Augmented fluoroscopy-guided endobronchial and transbronchial biopsy using endovascular steerable guiding sheaths in swine," Journal of Vascular and Interventional Radiology, vol. 31, No. 3, Mar. 2020, 2 pages.

Pritchett, M. et al., "Virtual or reality: divergence between preprocedural computer tomography scans and lunch anatomy during guided bronchoscopy," Journal of Thoracic Disease, vol. 12, No. 4, Apr. 2020, 17 pages.

Verhoeven, R. et al., "Predictive Value of Endobronchial Ultrasound Strain Elastography in Mediastinal Lymph Node Staging: The E-Predict Multicenter Study Results," Respiration, vol. 99, No. 6, Jun. 2020, 9 pages.

Yang, S. et al., "Augmented fluoroscopic bronchoscopy (AFB) versus percutaneous computed tomography-guided dye localization for thoracoscopic resection of small lung nodules: a propensity-matched study," Surgical Endoscopy, vol. 34, No. 12, Dec. 2020, 9 pages.

Verhoeven, R. et al., "Cone-Beam CT Image Guidance With and Without Electromagnetic Navigation Bronchoscopy for Biopsy of Peripheral Pulmonary Lesions," J Bronchology Interv Pulmonol, vol. 28, No. 1, Jan. 2021, 10 pages.

\* cited by examiner

METHOD AND SYSTEMS FOR MOTION-STABILIZED CLINICAL TOOL TRACKING AND VISUALIZATION

FIELD

Embodiments of the subject matter disclosed herein relate to x-ray imaging.

BACKGROUND

Imaging technologies such as x-ray imaging allow for non-invasive acquisition of images of internal structures or features of a subject or an object. Digital x-ray imaging systems produce digital data which can be reconstructed into radiographic images. In digital x-ray imaging systems, radiation from a source is directed toward the subject in a medical application, a package or baggage in a security screening application, or a fabricated component in an industrial quality control inspection application. A portion of the radiation passes through the subject/object and impacts a detector. The detector includes an array of discrete picture elements or detector pixels and generates output signals based upon the quantity or intensity of the radiation impacting each pixel region. The output signals are subsequently processed to generate an image that may be displayed for review. These images are used to identify and/or examine the internal structures and organs within a patient's body, objects within a package or container, or defects such as cracks within a fabricated component.

BRIEF DESCRIPTION

In one embodiment, a method of creating motion-adjusted images of a patient to guide an interventional medical procedure comprises acquiring a plurality of fluoroscopic images of an anatomy of interest in a patient, the plurality of fluoroscopic images depicting an interventional tool positioned relative to the anatomy of interest, segmenting the interventional tool in the plurality of fluoroscopic images, measuring motion of the patient in the plurality of fluoroscopic images, correcting the plurality of fluoroscopic images based on the motion of the patient, registering the segmented interventional tool to the anatomy of interest in the corrected plurality of fluoroscopic images, and displaying images with the segmented interventional tool registered to the anatomy of interest. In this way, a practitioner may view the position and movement of an interventional tool located within a patient relative to static images of the anatomy without motion artifacts or errors induced by patient motion such as respiratory motion or cardiac motion.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
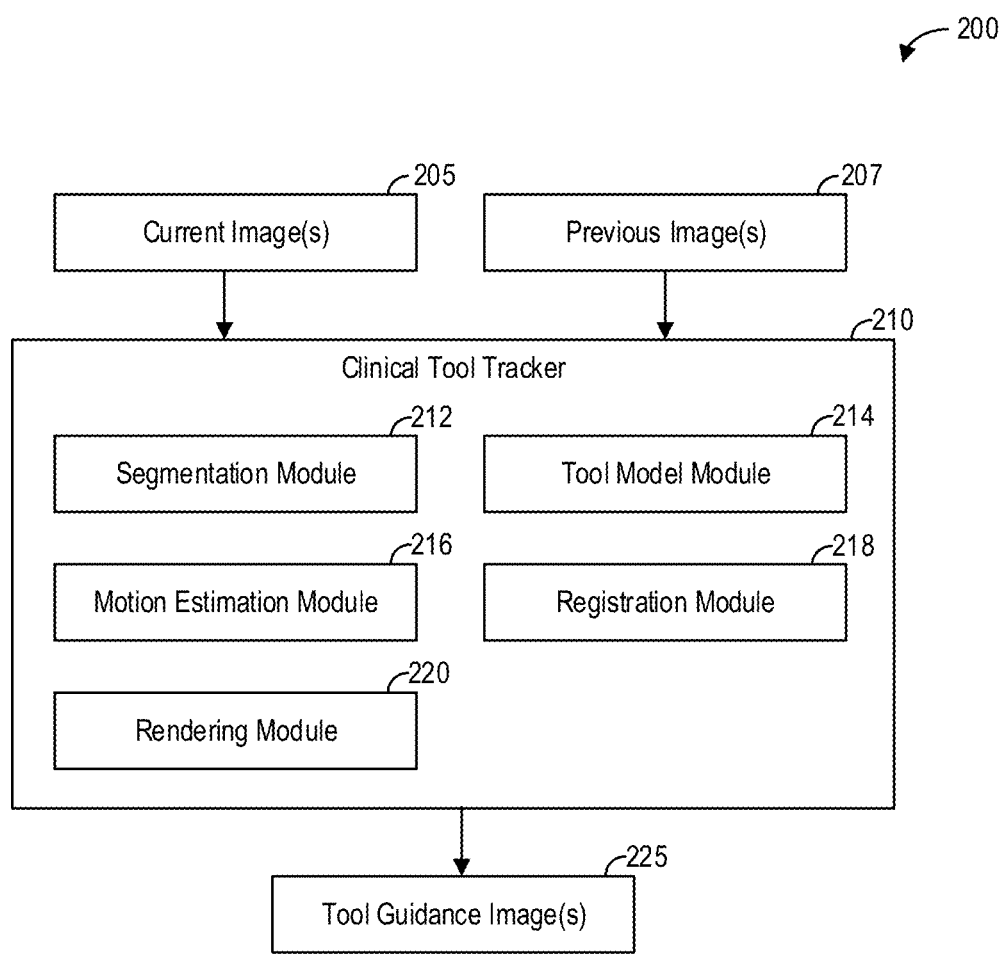
FIG. 2 shows a block diagram illustrating an example system for interventional tool tracking and guidance during fluoroscopic imaging according to an embodiment.
Figure 3:
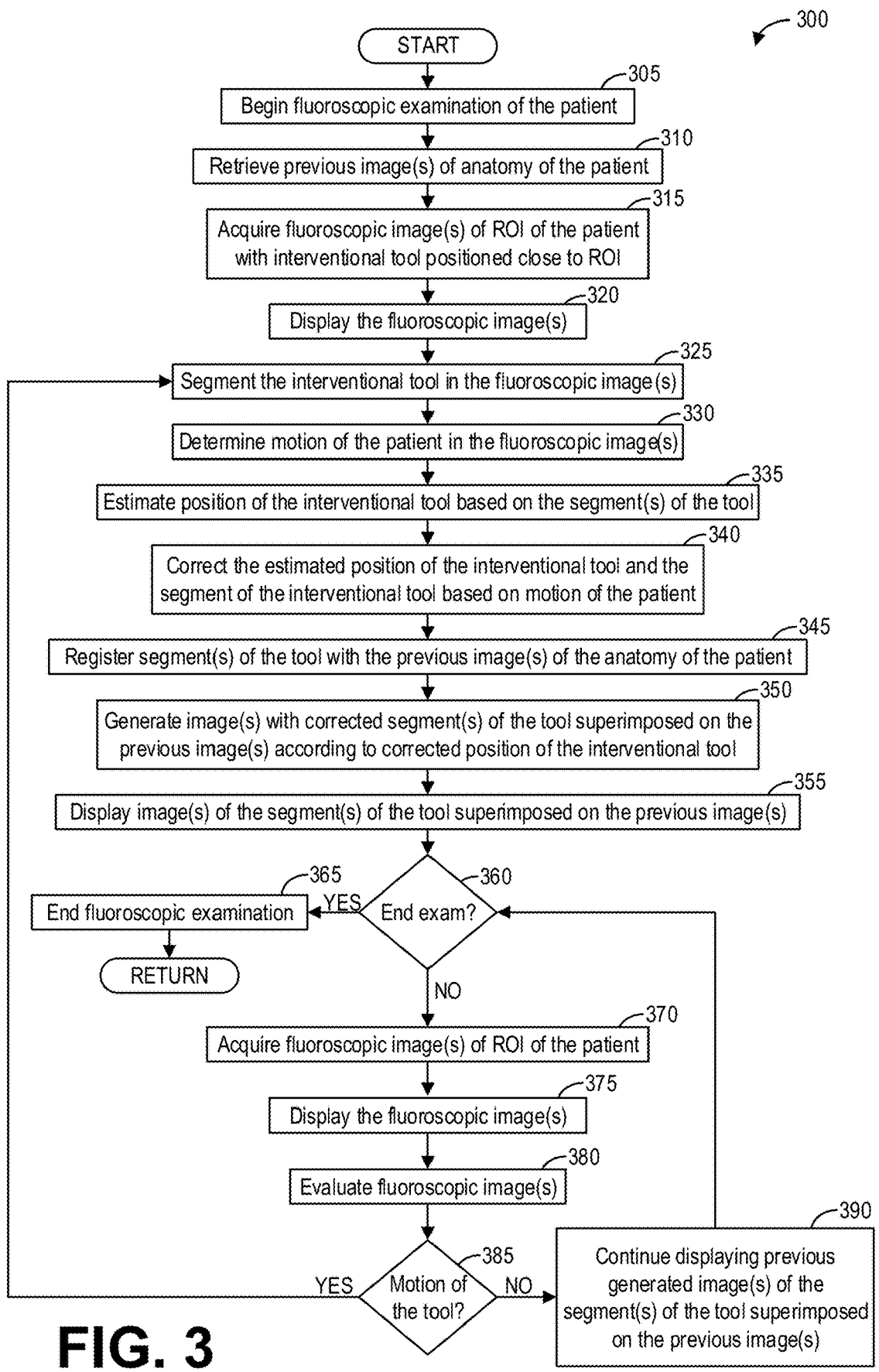
FIG. 3 shows a high-level flow chart illustrating an example method for interventional tool tracking and guidance according to an embodiment.
Figure 4:
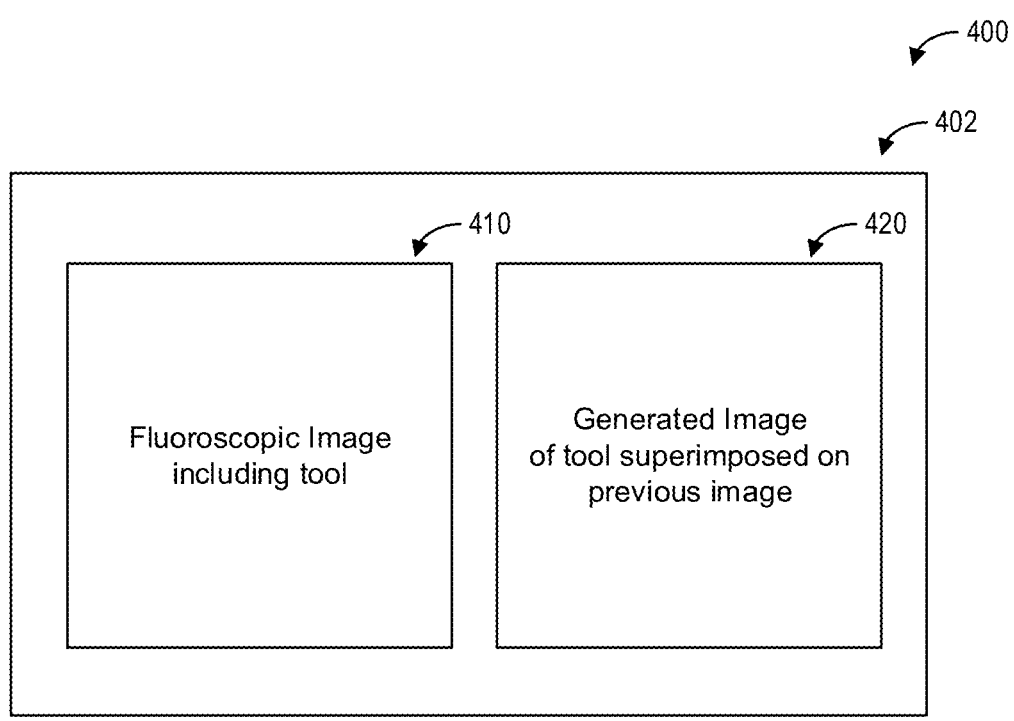
FIG. 4 shows a block diagram illustrating an example graphical user interface for displaying fluoroscopic images and interventional tool guidance according to an embodiment.
Figure 5:
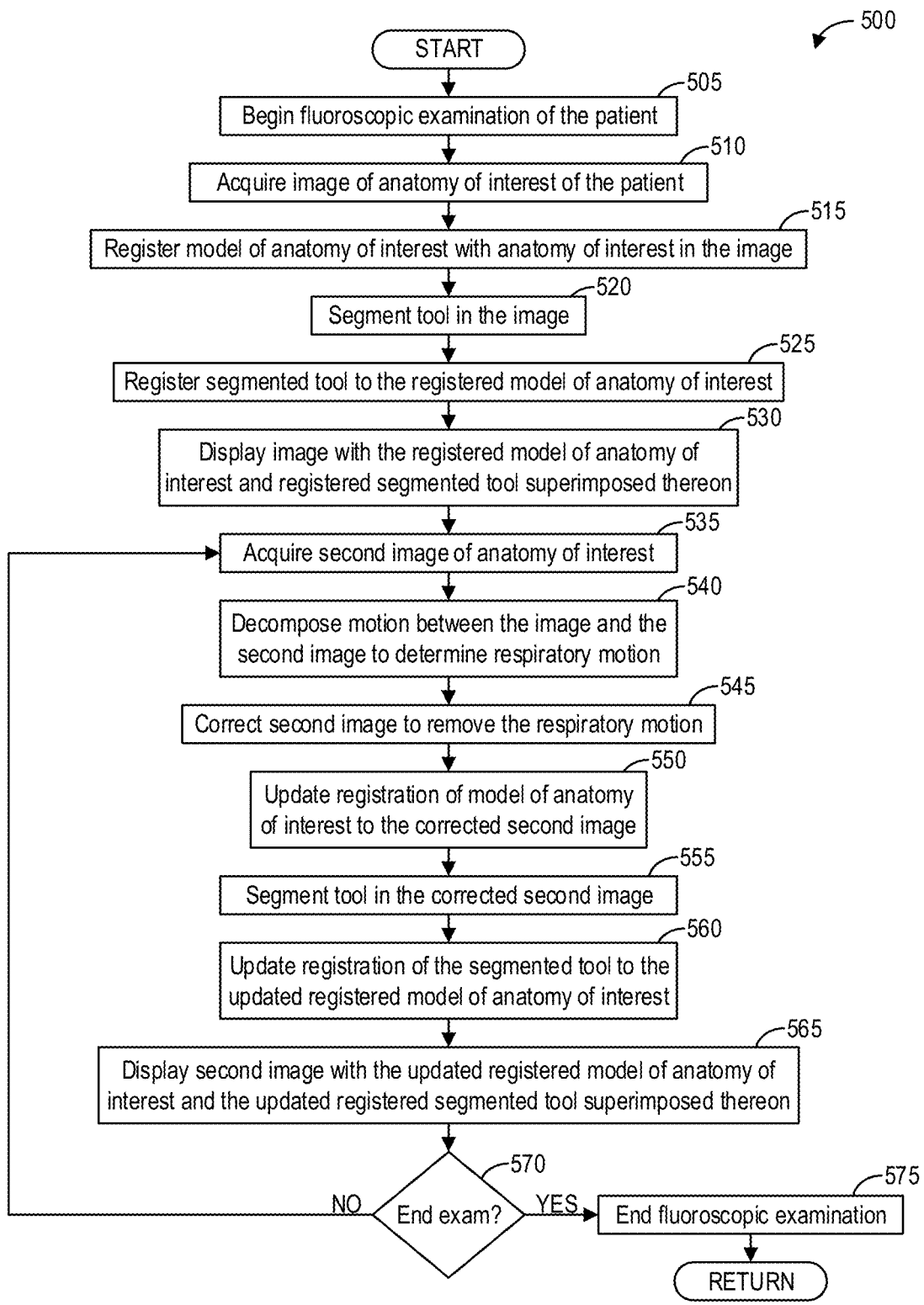
FIG. 5 shows a high-level flow chart illustrating an example method for stabilizing tool rendering according to an embodiment.
Figure 6:
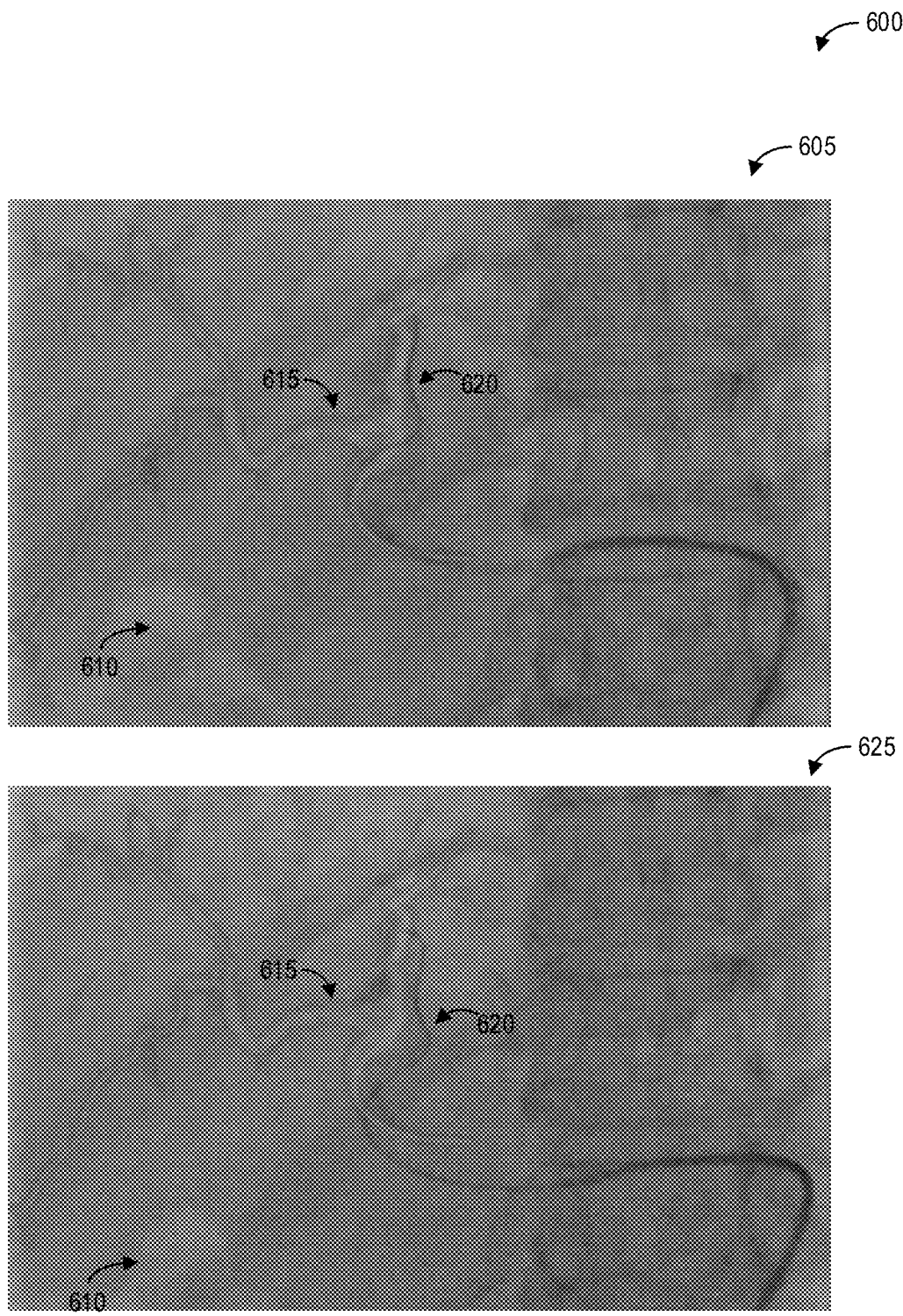
FIG. 6 shows a set of images illustrating destabilized position of an interventional tool in fluoroscopic imaging due to patient motion according to an embodiment.
Figure 7:
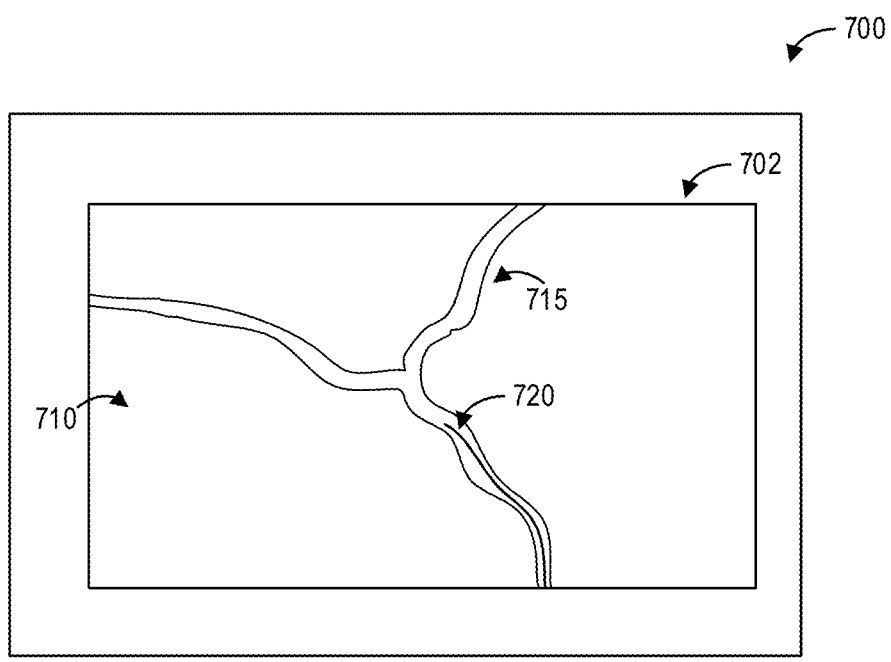
FIG. 7 shows a block diagram illustrating an example graphical user interface for displaying a stabilized tool rendering according to an embodiment.

The following description relates to various embodiments of x-ray imaging. In particular, systems and methods for motion-stabilized clinical tool tracking and visualization are provided. An x-ray imaging system, such as the x-ray imaging system depicted in FIG. 1, includes an x-ray detector which may be positioned relative to an x-ray source. The x-ray imaging system may include a clinical tool tracker, as depicted in FIG. 2, configured to create a stabilized rendering for tools navigation in fluoroscopy. The clinical tool tracker provides accurate fusion between a fluoroscopic sequence that moves with respiration and a static rendering of the anatomy. A method for motion-stabilized clinical tool tracking, as depicted in FIG. 3, includes tool segmentation, respiratory motion estimation, positioning segmented tools with respect to the anatomy of interest, and a dedicated rendering of tool motion. The images generated by the clinical tool tracker, as depicted in FIG. 4, provide a view where tool motion only corresponds to operator gestures and not respiratory motion, allowing the operator to simply assess their position with respect to the anatomy of interest. Another method for motion-stabilized clinical tool tracking, as depicted in FIG. 5, includes decomposing motion between images to determine patient motion such as respiratory or cardiac motion, and displaying images of a model of the anatomy of interest with segmented images of the interventional tool superimposed thereon. Without stabilizing the interventional tool, the position of the interventional tool drifts due to patient motion in displayed fluoroscopic images as shown in FIG. 6. By stabilizing the position of the imaged interventional tool relative to the model of the anatomy of interest, as depicted in FIG. 7, navigation of the interventional tool relative to the anatomy of interest is improved.

Figure 1:
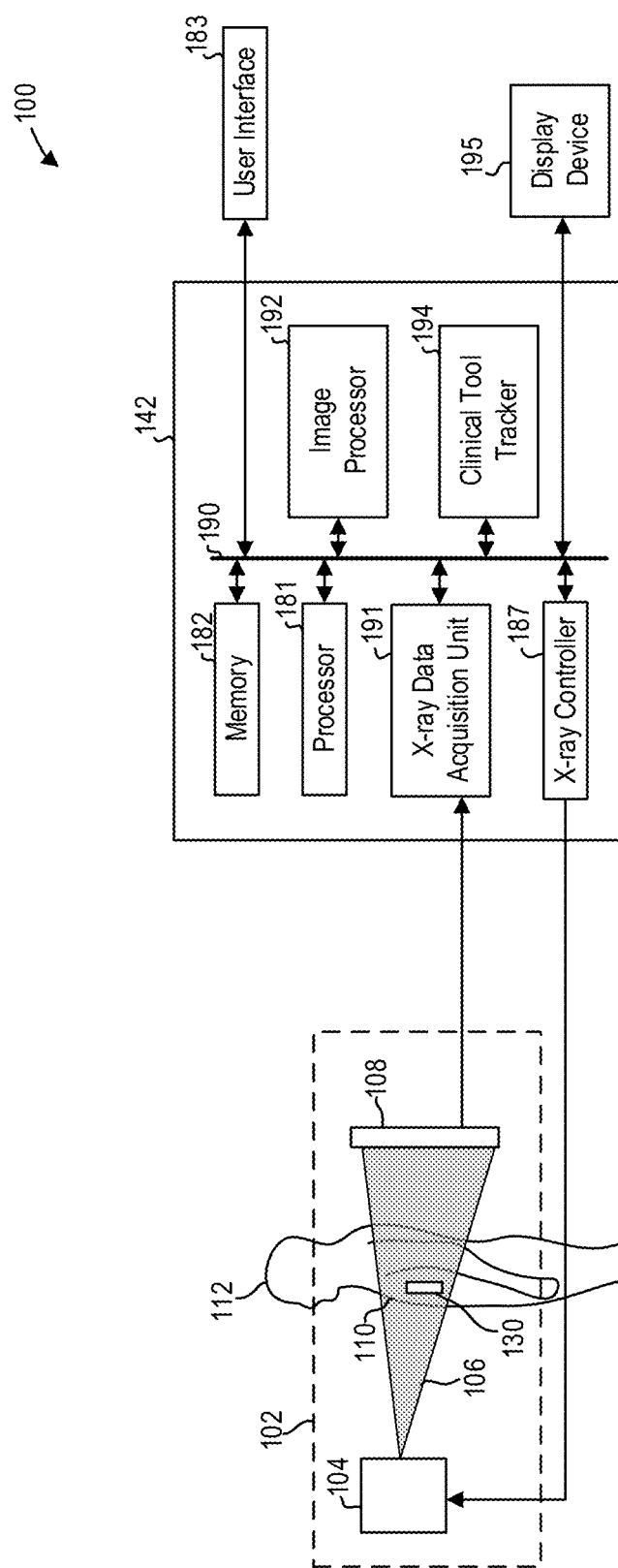
FIG. 1 shows an example x-ray imaging system according to an embodiment.

Turning now to FIG. 1, a block diagram of an x-ray imaging system 100 in accordance with an embodiment is shown. The x-ray imaging system 100 includes an image acquisition unit 102 and an operating console 142. The operating console 142 includes a processor 181, a memory 182, an x-ray controller 187, an x-ray data acquisition unit 191, an image processor 192, and a clinical tool tracker 194 for tracking and visualizing motion of a clinical tool 130 positioned within a subject 112. The operating console 142 is communicatively coupled to a user interface 183 and a display device 195, as depicted, though it should be appreciated that in some examples the operating console 142 may further comprise one or more of the user interface 183 and the display device 195. In some examples, the x-ray imaging system 100 comprises a mobile x-ray imaging system, such that the image acquisition unit 102 and the operating console 142 are portable or mobile.

The image acquisition unit 102 includes a radiation source such as an x-ray source 104. The x-ray source 104 is configured to emit a radiation beam such as an x-ray beam 106 having a field-of-view towards an object 110. In the example of FIG. 1, the object 110 is an anatomical region or a region of interest in a subject such as a patient 112. In another example, the object 110 may correspond to a package or a baggage in a security screening application. In yet another example, the object 110 may be a fabricated component in an industrial application. In some examples, the image acquisition unit 102 may further include a C-arm (not shown) wherein the x-ray source 104 and the x-ray detector 108 are mounted to opposite ends of the C-arm.

In some examples, the x-ray imaging system 100 further includes a patient table (not shown) configured to support the patient 112. The x-ray beam 106 upon impinging on the anatomical region 110 may be attenuated differently by portions of the anatomical region 110. An x-ray detector 108 that is disposed in the field-of-view of the x-ray beam 106 acquires the attenuated x-ray beam. The x-ray detector 108 may comprise, as non-limiting examples, an x-ray exposure monitor, an electric substrate, and so on. The x-ray detector 108 is moveable by an operator of the mobile x-ray imaging system 100 for manually positioning relative to the x-ray beam 106.

The operating console 142 comprises a processor 181, a memory 182, an x-ray controller 187, an x-ray data acquisition unit 191, an image processor 192, and a grid artifact correction unit 193. X-ray image data acquired by the x-ray detector 108 is transmitted from the x-ray detector 108 and is received by the x-ray data acquisition unit 191. The collected x-ray image data are image-processed by the image processor 192. A display device 195 communicatively coupled to the operating console 142 displays an image-processed x-ray image thereon. The x-ray controller 187 supplies power of a suitable voltage current to the x-ray source 104 for powering the x-ray source 104.

The image acquisition unit 102 is further configured to generate an x-ray image corresponding to the object 110 based on the detected x-ray beam. In the example of FIG. 1, the x-ray image is a projection of the anatomical region 110 of the subject 112 in a detector plane of the x-ray detector 108.

The image processor 192 is communicatively coupled to the x-ray data acquisition unit 191 and configured to receive the x-ray image from the x-ray data acquisition unit 191. In some examples, the image processor 192 is configured to identify a medical condition of the anatomical region 110 of the subject 112 based on the x-ray image. In one embodiment, the image processor 192 is configured to display the x-ray image, the identified medical condition, or a combination thereof on the display device 195. To that end, the image processor 192 processes the x-ray image with one or more image processing techniques, including but not limited to segmentation techniques, deep learning techniques, and so on.

In some examples, the display device 195 may be integrated with the user interface 183. For example, the display device 195 may comprise a touch-sensitive display device or a touchscreen, such that the display device 195 may display a graphical user interface and detect inputs by an operator.

Further, the processor 181 is communicatively coupled to the memory unit 182, the image processor 192, and the clinical tool tracker 194 via a communication bus 190 and configured to provide computing and control functionalities. The processor 181 includes at least one of a central processing unit (CPU), a graphics processing unit (GPU), a digital signal processor, and a controller. In other embodiments, the processor 181 includes a customized processor element such as, but not limited to, an application-specific integrated circuit (ASIC) and a field-programmable gate array (FPGA). The processor 181 may be further configured to receive commands and/or parameters from an operator via the user interface 183. In some embodiments, the processor 181 may perform one or more functions of at least one of the image processor 192 and the clinical tool tracker 194. The processor 181 may include more than one processor cooperatively working with each other for performing the functions described herein. The processor 181 may also be configured to store and retrieve contents into and from the memory 182. In one example, the processor 181 is configured to initiate and control the functionality of at least one of the image acquisition unit 102 and the clinical tool tracker 194.

In one embodiment, the memory 182 comprises a random-access memory (RAM), read-only memory (ROM), flash memory, or any other type of computer-readable memory accessible by one or more of the image acquisition unit 102, the clinical tool tracker 194, the image processor 192, and the processor 181. Also, in some examples, the memory 182 comprises a non-transitory computer-readable medium encoded with a program having a plurality of instructions to instruct at least one of the image acquisition unit 102, the clinical tool tracker 194, the image processor 192, and the processor 181 to perform a sequence of steps to generate the x-ray image. The program may further instruct the display device 195 to display the x-ray image to the operator for evaluation of the x-ray image.

As an illustrative example, FIG. 2 shows a block diagram illustrating an example system 200 for interventional tool tracking and guidance according to an embodiment. In particular, method 200 relates to tracking an interventional tool with a clinical tool tracker 210. The clinical tool tracker 210 may comprise the clinical tool tracker 194 of the x-ray imaging system 100, for example.

Current image(s) 205 and previous image(s) 207 are provided to the clinical tool tracker 210. The current image(s) 205 comprise fluoroscopic image(s) acquired via an x-ray image acquisition unit 102. The clinical tool tracker 210 processes the current image(s) 205 to locate an interventional tool, such as the interventional tool 130, within the current image(s) 205 and track the motion of the interventional tool over time. The clinical tool tracker 210 further generates guidance image(s) by superimposing segmented image(s) of the interventional tool on the previous image(s) 207. The previous image(s) 207 may comprise two-dimensional or three-dimensional images of patient anatomy acquired prior to the fluoroscopic examination wherein the current image(s) 205 are acquired, and the previous image(s) may be static or dynamic. The previous image(s) 207 may comprise projective renderings of a 3D segmented object, previous recorded images (such as vessel road maps, digitally subtracted angiography, contrast agent injection sequences), image manual annotations, pre-operative volume projections, and so on. The previous image(s) 207 may be acquired via a fluoroscopic imaging mode, for example, or one or more imaging modes of the x-ray imaging system 100 other than a fluoroscopic imaging mode.

The clinical tool tracker 210 comprises a segmentation module 212, a tool model module 214, a motion estimation module 216, a registration module 218, and a rendering module 220. The segmentation module 212 is configured to segment clinical tools or interventional tools in the current image(s) 205. The tool model module 214 models the orientation, position, and motion of the interventional tool(s) in the current image(s) 205 over time. The motion estimation module 216 estimates motion in the current image(s) 205 caused by patient motion, such as respiratory motion or other motion. The motion estimation module 216 further estimates motion of the interventional tool(s) in the current image(s) 205. The segmentation of the interventional tool by the segmentation module 212 may be used to estimate motion with respect to static segmented anatomy of the patient. The tool model module 214 may update or correct the tool model based on the estimated patient motion as well as the estimated tool motion. The registration module 218 registers the segmented interventional tool with the previous image(s) 207 of the patient anatomy. The rendering module 220 renders or generates images that depict the movement of the interventional tool relative to the previous image(s) 207 without changes induced by patient respiratory motion. The generated image(s) of the rendering module 220 are output as tool guidance image(s) 225. The tool guidance image(s) 225 depict an image with a merged position of the segmented interventional tool(s) and the previously-acquired images of the patient anatomy to the practitioner or operator, where the image changes induced by patient respiratory motion are removed.

The ROI may be in close proximity to patient anatomy used for interventional tool insertion. The ROI may comprise, as illustrative and non-limiting examples, a tumor or biopsy target, an embolization target, and so on. The patient anatomy used for interventional tool insertion may comprise vasculature or bronchia, as illustrative and non-limiting examples.

Thus, as discussed further herein, a method of creating motion-adjusted images of a patient to guide an interventional medical procedure comprises acquiring a plurality of fluoroscopic images of an ROI of a patient having an interventional tool positioned close to the ROI, processing the plurality of fluoroscopic images to segment the interventional tool, further processing the plurality of fluoroscopic images to determine motion of the patient, estimating motion with respect to a static segmented anatomy of the patient based on the segmentation of the interventional tool, registering the segmented interventional tool with previously-acquired images of the patient anatomy, and displaying an image with merged position of the segmented interventional tool and the previously-acquired static images of the patient anatomy to a practitioner where the image changes induced by patient respiratory motion are removed. In an example, the registering only occurs after the motion is determined and corrected, where the motion is determined and corrected only after the interventional tool has been segmented. In this way, the image processing can occur faster for a given processing capability as it can be more efficient to measure and correct for motion after segmentation, even with additional operations such as registration.

FIG. 3 shows a high-level flow chart illustrating an example method 300 for interventional tool tracking and guidance according to an embodiment. In particular, method 300 relates to automatically tracking an interventional tool in fluoroscopic images and displaying a position of the interventional tool for guiding an operator during fluoroscopic imaging. Method 300 is described with regard to the systems and components of FIGS. 1 and 2, though it should be appreciated that the method may be implemented with other systems and components without departing from the scope of the present disclosure. Method 300 may be implemented as executable instructions in non-transitory memory, such as memory 182, and may be executed by a processor, including one or more of the processor 181, the image processor 192, or the clinical tool tracker 194, of an x-ray imaging system, such as the x-ray imaging system 100.

Method 300 begins at 305. At 305, method 300 begins a fluoroscopic examination of the patient. For example, during a fluoroscopic examination, method 300 controls the x-ray source 104 and the x-ray detector 108, for example via the x-ray controller 187 and the x-ray data acquisition unit 191, to acquire a series of fluoroscopic images of the subject or patient 112. During the fluoroscopic examination, a clinical tool or interventional tool 130, which may comprise a medical needle, guidewire, catheter, biopsy instrument, pedicle screw, probe, or another surgical tool or instrument, is inserted or applied to an anatomy of interest or region of interest such as the object 110. The fluoroscopic imaging of the interventional tool 130 thus enables navigation under fluoroscopic guidance where an anatomical structure of interest is not visible (e.g., because the anatomical structure of interest is internal to the patient). Thus, to begin a fluoroscopic examination of the patient, method 300 may initiate control of the x-ray source 104 and the x-ray detector 108. In some examples, beginning the fluoroscopic examination of the patient may include one or more of receiving an indication of the patient, desired settings for fluoroscopic imaging, an indication of an anatomy of interest, a selection of one or more previous image(s) of the anatomy of interest, and so on. Further, beginning the fluoroscopic examination of the patient may include acquiring at least one fluoroscopic image of the patient.

At 310, method 300 retrieves one or more previous image(s) of anatomy of the patient. For example, method 300 may retrieve one or more previous image(s) of the anatomy of interest of the patient from non-transitory memory 182, for example based on an indication of the patient and/or the anatomy of interest received during initialization of the fluoroscopic examination. The one or more previous image(s) may comprise a static rendering of the anatomy of interest, and thus may comprise a projective rendering of a three-dimensional object (e.g., the anatomy of interest), a roadmap acquisition, or another image of the anatomy of interest acquired by a suitable imaging modality (e.g., fluoroscopic imaging, non-fluoroscopic x-ray imaging, CT imaging, and so on). As discussed further herein, an image of the interventional tool may be superimposed on the one or more previous image(s) to provide guidance for an operator of the imaging system.

At 315, method 300 acquires fluoroscopic image(s) of an ROI of the patient with an interventional tool positioned close to the ROI. For example, method 300 controls the x-ray source 104 and the x-ray detector 108, for example via the x-ray controller 187 and the x-ray data acquisition unit 191, to acquire at least one fluoroscopic image of the subject or patient 112. At 320, method 300 displays the fluoroscopic image(s), for example via a display device such as the display device 195.

At 325, method 300 segments the interventional tool in the fluoroscopic image(s). For example, method 300 processes, with the image processor 192 and/or the clinical tool tracker 194 for example, the fluoroscopic image(s) acquired at 315 to segment the interventional tool in the fluoroscopic image(s). Method 300 may use any suitable segmentation method such as thresholding, clustering, motion-based segmentation, histogram-based thresholding, edge detection, machine learning-based segmentation, and so on, or a combination thereof. Method 300 thus obtains at least one segmented image of the interventional tool in the fluoroscopic image(s). The at least one segmented image may comprise a selection of pixels in the fluoroscopic image(s) corresponding to the interventional tool, or alternatively may comprise a distinct image comprising the pixels in the fluoroscopic image(s) corresponding to the interventional tool.

At 330, method 300 determines motion of the patient in the fluoroscopic image(s). Method 300 may determine motion of the patient in the fluoroscopic image(s) by measuring, as an illustrative and non-limiting example, optical flow between two or more fluoroscopic images including the fluoroscopic image(s), where the optical flow indicates relative motion of objects depicted in the fluoroscopic image(s) such as tissue or other anatomy and the interventional tool in the fluoroscopic image(s) relative to one or more previous fluoroscopic image(s). For example, method 300 may determine motion of the patient in the fluoroscopic image(s) relative to an initial fluoroscopic image acquired during initialization of the fluoroscopic examination at 305 during a first iteration, and may determine motion of the patient in the fluoroscopic image(s) relative to a fluoroscopic image acquired at 315 during a previous iteration. To determine motion of the patient in the fluoroscopic image(s) and thus distinguish the motion of the patient from motion of the interventional tool, method 300 may decompose or filter the determined motion to identify low-frequency motion which may correspond to respiratory motion (e.g., motion of tissue or other anatomy in the patient caused by respiration of the patient).

At 335, method 300 estimates a position of the interventional tool based on the segment(s) of the tool in the fluoroscopic image(s). At 340, method 300 corrects the estimated position of the interventional tool and the segment(s) of the interventional tool based on the motion of the patient. For example, method 300 may correct the estimated position of the interventional tool and thus the segment(s) of the interventional tool in the fluoroscopic image(s) by removing the motion of the patient, specifically respiratory motion identified at 330. At 345, method 300 registers the corrected segment(s) of the tool with the previous image(s) of the anatomy of the patient. Specifically, method 300 registers the corrected segment(s) of the interventional tool to the anatomy of interest in the previous image(s) wherein the interventional tool is positioned. At 350, method 300 generates one or more image(s) with the corrected segment(s) of the tool superimposed on the previous image(s) according to the corrected position of the interventional tool. By correcting the segment(s) of the interventional tool and registering the corrected segment(s) of the interventional tool to the anatomy of interest, the generated image(s) with the corrected segment(s) superimposed on the previous image(s) according to the corrected position of the interventional tool comprises a stabilized view of the interventional tool relative to the anatomy of interest. At 355, method 300 displays the one or more image(s) of the segment(s) of the tool superimposed on the previous image(s), for example, via the display device 195. In some examples, the one or more image(s) may be positioned adjacent to the corresponding fluoroscopic image(s) in a graphical user interface displayed via the display device 195, such that a user may view the fluoroscopic image(s) and the stabilized view of the interventional tool simultaneously. In this way, the user may discern the position of the interventional tool relative to the anatomy of interest as the user moves the interventional tool relative to the anatomy of interest while also discerning the impact of patient motion depicted in the fluoroscopic image(s) on the position of the interventional tool and the anatomy of interest, such that navigation of the interventional tool relative to the anatomy of interest is improved.

At 360, method 300 determines whether a command to end the fluoroscopic examination is received. A command to end the fluoroscopic examination may be received, for example, via the user interface 183. If a command to end the fluoroscopic examination is received ("YES"), method 300 proceeds to 365, wherein method 300 ends the fluoroscopic examination. Method 300 ends the fluoroscopic examination by ceasing control of the x-ray source 104 and the x-ray detector 108 to acquire fluoroscopic images. Method 300 then returns.

However, referring again to 360, if a command to end the fluoroscopic examination is not received ("NO"), method 300 proceeds to 370. At 370, method 300 acquires fluoroscopic image(s) of the ROI of the patient. At 375, method 300 displays the fluoroscopic image(s) via the display device 195. At 380, method 300 evaluates the fluoroscopic image (s). Method 300 may evaluate the fluoroscopic image(s) acquired at 370 relative to the fluoroscopic image(s) acquired at 315, for example, or to fluoroscopic image(s) previously acquired at 370 during a preceding iteration, to determine motion of the interventional tool. Method 300 may determine motion of the interventional tool according to any apparent motion of the interventional tool between the fluoroscopic images, or may decompose the motion between the fluoroscopic images to determine non-respiratory motion corresponding to motion of the interventional tool.

At 385, method 300 determines whether the fluoroscopic image(s) acquired at 370 indicate motion of the interventional tool. If there is no motion of the interventional tool ("NO"), method 300 continues to 390. At 390, method 300 continues displaying the previous generated image(s) of the segment(s) of the tool superimposed on the previous image(s). Method 300 then continues to 360, wherein method 300 determines whether there is a command to end the fluoroscopic examination. Thus, while the interventional tool is not moving, method 300 continues to acquire and display fluoroscopic image(s) without updating the stabilized interventional tool guidance image(s).

Referring again to 385, if the fluoroscopic image(s) acquired at 370 indicate motion of the interventional tool ("YES"), method 300 returns to 325 to segment the interventional tool in the fluoroscopic image(s) acquired at 370. Method 300 thus continues to determine motion of the patient in the fluoroscopic image(s) at 330, estimate the position of the interventional tool at 335, and so on, to generate updated image(s) with segment(s) of the interventional tool superimposed on the previous image(s) with corrections applied to account for patient motion such as respiratory motion.

As an illustrative example, FIG. 4 shows a block diagram illustrating an example graphical user interface 400 including an image display area 402 displaying fluoroscopic images 410 and interventional tool guidance 420 according to an embodiment. As discussed hereinabove with regard to FIG. 3, a stabilized image of an interventional tool may be generated during a fluoroscopic examination to provide guidance to a user navigating the interventional tool relative to an anatomy of interest within a patient. The graphical user interface 400 may thus display fluoroscopic images including the interventional tool such as the fluoroscopic image 410, and may further display an image of the interventional tool stabilized relative to the anatomy of interest, such as the generated image 420 of the tool superimposed on a previous image.

As another illustrative and non-limiting example of how imaging of interventional tools may be stabilized during an examination to improve guidance and navigation, FIG. 5 shows a high-level flow chart illustrating an example method 500 for stabilizing tool rendering according to an embodiment. In particular, method 500 relates to automatically tracking an interventional tool in fluoroscopic images and displaying a stabilized position of the interventional tool with respect to an anatomy of interest for guiding an operator during fluoroscopic imaging. Method 500 is described with regard to the systems and components of FIGS. 1 and 2, though it should be appreciated that the method may be implemented with other systems and components without departing from the scope of the present disclosure. Method 500 may be implemented as executable instructions in non-transitory memory, such as memory 182, and may be executed by a processor, including one or more of the processor 181, the image processor 192, or the clinical tool tracker 194, of an x-ray imaging system, such as the x-ray imaging system 100.

Method 500 begins at 505. At 505, method 500 begins a fluoroscopic examination of a patient. For example, as discussed hereinabove, during a fluoroscopic examination, method 500 controls the x-ray source 104 and the x-ray detector 108, for example via the x-ray controller 187 and the x-ray data acquisition unit 191, to acquire a series of fluoroscopic images of the subject or patient 112. During the fluoroscopic examination, a clinical tool or interventional tool 130, which may comprise a medical needle, guidewire, catheter, biopsy instrument, pedicle screw, probe, or another surgical tool or instrument, is inserted or applied to an anatomy of interest or region of interest such as the object 110. The fluoroscopic imaging of the interventional tool 130 thus enables navigation under fluoroscopic guidance where an anatomical structure of interest is not visible (e.g., because the anatomical structure of interest is internal to the patient). Thus, to begin a fluoroscopic examination of the patient, method 500 may initiate control of the x-ray source 104 and the x-ray detector 108. In some examples, beginning the fluoroscopic examination of the patient may include one or more of receiving an indication of the patient, desired settings for fluoroscopic imaging, an indication of an anatomy of interest, a selection of one or more previous image(s) of the anatomy of interest, and so on. Further, beginning the fluoroscopic examination of the patient may include acquiring at least one fluoroscopic image of the patient.

At 510, method 500 acquires an image of an anatomy of interest of the patient. For example, method 500 controls the x-ray source 104 and the x-ray detector 108, for example via the x-ray controller 187 and the x-ray data acquisition unit 191, to acquire an image such as a fluoroscopic image of the anatomy of interest. The anatomy of interest may comprise, as illustrative and non-limiting examples, a tumor, vessels, or another anatomical structure that may be the target of the interventional tool.

At 515, method 500 registers a model of the anatomy of interest with the anatomy of interest in the image. The model may comprise a projection of a three-dimensional model of the anatomy of interest in the plane of the image acquired at 510, as an illustrative and non-limiting example, wherein the model may be generated or adapted to the anatomy of interest in the image acquired at 510. The model may alternatively comprise a projection of a three-dimensional segmented image volume of the anatomy of interest, for example acquired via a three-dimensional imaging modality such as CT. As yet another example, the model may comprise another static rendering of the anatomy of interest obtained from a roadmap acquisition or another type of prior image of the anatomy of interest acquired prior to the fluoroscopic examination. Method 500 registers the model of the anatomy of interest to the corresponding anatomy of interest in the image so that the position and orientation of the model of the anatomy of interest corresponds to the position and orientation of the anatomy of interest in the image.

At 520, method 500 segments an interventional tool in the image acquired at 510. For example, method 500 processes, with the image processor 192 and/or the clinical tool tracker 194 for example, the fluoroscopic image(s) acquired at 315 to segment the interventional tool in the fluoroscopic image(s). Method 500 may use any suitable segmentation method such as thresholding, clustering, motion-based segmentation, histogram-based thresholding, edge detection, machine learning-based segmentation, and so on, or a combination thereof. Method 500 thus obtains at least one segmented image of the interventional tool in the fluoroscopic image(s). The at least one segmented image may comprise a selection of pixels in the fluoroscopic image(s) corresponding to the interventional tool, or alternatively may comprise a distinct image comprising the pixels in the fluoroscopic image(s) corresponding to the interventional tool.

At 525, method 500 registers the segmented tool to the registered model of the anatomy of interest. Method 500 may register the segmented tool to the registered model of the anatomy of interest, for example, by imposing boundaries for the segmented tool such that the segmented tool is positioned within the anatomy of interest, for example if the anatomy of interest is a vessel through which the interventional tool is being guided. Similarly, for other anatomies of interest, the position of the interventional tool may be registered to the position of the registered model so that the relative positions do not shift when accounting for respiratory motion or other patient motion as discussed further herein.

At 530, method 500 displays an image with the registered model of the anatomy of interest and the registered segmented tool superimposed thereon, for example via the display device 195. The image may comprise the fluoroscopic image acquired at 510, for example, or may comprise a previous image of the anatomy of interest acquired via the x-ray imaging system 100 or another imaging modality. Alternatively, the image may comprise only the registered model of the anatomy of interest and the registered segmented tool superimposed thereon, in some examples, such that the image does not include other anatomical structures or tissue.

At 535, method 500 acquires a second image of the anatomy of interest. For example, method 500 controls the x-ray source 104 and the x-ray detector 108, for example via the x-ray controller 187 and the x-ray data acquisition unit 191, to acquire the second image. At 540, method 500 decomposes motion between the image and the second image to determine respiratory motion between the images. For example, method 500 may determine motion of the patient between the image and the second image by measuring, as an illustrative and non-limiting example, optical flow between the two images, where the optical flow indicates relative motion of objects depicted in the second image such as tissue or other anatomy and the interventional tool relative to the image. Method 500 may then decompose the determined motion and remove low-frequency components of the determined corresponding to patient motion such as respiratory motion or cardiac motion. Continuing at 545, method 500 corrects the second image based on the patient motion such as respiratory or cardiac motion. In an example, the correction removes all of the measured motion, or a portion of the measured motion. In some examples, the second image may be corrected via image registration techniques such as optical flow algorithms. In other examples, second image may be corrected by registering the segmented tool itself, decomposing the motion into respiratory, cardiac, and/or navigation components, and removing the respiratory and cardiac components of the motion to stabilize the object. Method 500 then updates at 550 the registration of the model of the anatomy of interest to the anatomy of interest in the corrected second image.

At 555, method 500 segments the interventional tool in the corrected second image using a suitable segmentation method as described hereinabove. Then, at 560, method 500 updates the registration of the segmented tool to the updated registered model of the anatomy of interest. At 565, method 500 displays a second image with the updated registered model of the anatomy of interest and the updated registered segmented tool superimposed thereon, wherein the second image may comprise the second image acquired at 535 or another static image as described hereinabove.

At 570, method 500 determines whether to end the fluoroscopic examination. If the examination is not ending ("NO"), method 500 returns to 535 to acquire an additional image of the anatomy of interest, such as a third image. At 540, method 500 then decomposes motion between the third image and the second image to determine respiratory motion between the third image and the second image. Method 500 thus continues to correct for respiratory motion between images and update the registration of the model and the interventional tool accordingly during the fluoroscopic examination, until method 500 determines to end the examination at 570. Once method 500 determines to end the examination at 570 ("YES"), method 500 continues to 575, where method 500 ends the fluoroscopic examination. Method 500 then returns.

As an illustrative example of interventional tool guidance without stabilization, FIG. 6 shows a set of images 600 illustrating destabilized position of an interventional tool in fluoroscopic imaging due to patient motion. In a first image 605 of the set of images 600, a model 615 of an anatomy of interest (e.g., a vessel) is displayed over a fluoroscopic image, and an interventional tool 620 (e.g., a guidewire) is depicted as within the anatomy of interest illustrated via the model 615. Displaying the model 615 enhances the visualization of the anatomy of interest which may not be as visible via fluoroscopic imaging, which may be calibrated to image the interventional tool itself. Thus, superimposing the model 615 onto the image 605 enables a user to visualize the position of the interventional tool 620 relative to the anatomy of interest depicted by the model 615. However, due to respiratory motion, the position of tissue 610 depicted in the image 605 shifts to a different position in a subsequent image 625. The respiratory motion further causes the anatomy of interest to shift, and so the position of the interventional tool 620 in the subsequent image 625 shifts as well. If the relative positions of the interventional tool 620 and the model 615 are not stabilized, the position of the interventional tool 620 shifts with patient motion in the acquired fluoroscopic images. By segmenting and registering the interventional tool 620 to the model 615 as discussed hereinabove with regard to FIGS. 3 and 5, a stabilized view of the interventional tool relative to the anatomy of interest may be provided to the user.

For example, FIG. 7 shows a block diagram illustrating an example graphical user interface 700 for displaying a stabilized tool rendering according to an embodiment. The graphical user interface 700 may be displayed via a display device 195, for example, and depicts an image 702 of a model 715 of the anatomy of interest with a segmented image 720 of the interventional tool superimposed thereon. Optionally, the image 702 may include a fluoroscopic image or a static image depicting tissue 710 or other anatomical structures, wherein the model 715 and the segmented interventional tool 720 are superimposed thereon. Alternatively, as discussed hereinabove with regard to FIG. 4, fluoroscopic images may be depicted in the graphical user interface 700 in a position adjacent to the image 702 so that the user may view the acquired fluoroscopic images, while the image 702 is updated according to motion of the interventional tool to visualize the motion of the interventional tool relative to the anatomy of interest depicted by the model 715.

A technical effect of the present disclosure includes the display of a motion-stabilized clinical tool that is inserted into an anatomy of interest in a patient. Another technical effect of the present disclosure is the motion correction of images to remove respiratory and/or cardiac motion. Yet another technical effect of the present disclosure is the acquisition of fluoroscopic images, the correction of such fluoroscopic images for patient motion, and the display of such corrected fluoroscopic images with a stabilized view of an interventional tool depicted in the corrected fluoroscopic images.

In one embodiment, a method comprises acquiring a plurality of fluoroscopic images of an anatomy of interest in a patient, the plurality of fluoroscopic images depicting an interventional tool positioned relative to the anatomy of interest, segmenting the interventional tool in the plurality of fluoroscopic images, measuring motion of the patient in the plurality of fluoroscopic images, correcting the plurality of fluoroscopic images to remove the motion of the patient, registering the segmented interventional tool to the anatomy of interest in the corrected plurality of fluoroscopic images, and displaying images with the segmented interventional tool registered to the anatomy of interest.

In a first example of the method, measuring the motion of the patient in the plurality of fluoroscopic images comprises measuring low-frequency motion between a first fluoroscopic image and a second fluoroscopic image of the plurality of fluoroscopic images. In a second example of the method optionally including the first example, correcting the plurality of fluoroscopic images to remove the motion of the patient comprises subtracting the low-frequency motion from the second fluoroscopic image. In a third example of the method optionally including one or more of the first and second examples, the method further comprises registering a model of the anatomy of interest to the anatomy of interest in the plurality of fluoroscopic images. In a fourth example of the method optionally including one or more of the first through third examples, the method further comprises retrieving a prior image of the anatomy of interest, and determining the model of the anatomy of interest according to the prior image of the anatomy of interest. In a fifth example of the method optionally including one or more of the first through fourth examples, the prior image comprises a three-dimensional image volume, and wherein the model of the anatomy of interest comprises a projection of a three-dimensional model of the anatomy of interest in a plane of the plurality of fluoroscopic images, the three-dimensional model of the anatomy of interest determined from the three-dimensional image volume. In a sixth example of the method optionally including one or more of the first through fifth examples, registering the segmented interventional tool to the anatomy of interest in the corrected plurality of fluoroscopic images comprises registering the segmented interventional tool to the model of the anatomy of interest. In a seventh example of the method optionally including one or more of the first through sixth examples, displaying the images with the segmented interventional tool registered to the anatomy of interest comprises displaying motion-stabilized views of the segmented interventional tool superimposed on the model of the anatomy of interest. In an eighth example of the method optionally including one or more of the first through seventh examples, the anatomy of interest comprises a tumor or a vessel, and wherein the motion of the patient comprises one or more of respiratory motion and cardiac motion.

In another embodiment, a method comprises acquiring a series of fluoroscopic images of an anatomy of interest in a patient, the series of fluoroscopic images depicting an interventional tool positioned relative to the anatomy of interest, and while acquiring the series of fluoroscopic images: segmenting the interventional tool in the series of fluoroscopic images; determining motion between a first fluoroscopic image and second fluoroscopic image of the series of fluoroscopic images; decomposing the motion into motion of the patient and motion of the interventional tool; correcting the second fluoroscopic image to remove the motion of the patient; registering the segmented interventional tool to the anatomy of interest in the corrected second fluoroscopic image; and displaying an image with the registered segmented interventional tool superimposed on the anatomy of interest.

In a first example of the method, the method further comprises determining a model of the anatomy of interest and registering the model of the anatomy of interest to the anatomy of interest in the corrected second fluoroscopic image. In a second example of the method optionally including the first example, registering the segmented interventional tool to the anatomy of interest in the corrected second fluoroscopic image comprises registering the segmented interventional tool to the registered model of the anatomy of interest. In a third example of the method optionally including one or more of the first and second examples, displaying the image with the registered segmented interventional tool superimposed on the anatomy of interest comprises displaying the image with the registered segmented interventional tool superimposed on the registered model of the anatomy of interest. In a fourth example of the method optionally including one or more of the first through third examples, the method further comprises updating the image of the registered segmented interventional tool superimposed on the anatomy of interest according to motion of the interventional tool in fluoroscopic images acquired subsequent to the second fluoroscopic image, and displaying the updated image.

In yet another embodiment, a system comprises an x-ray source configured to generate x-rays, an x-ray detector configured to detect the x-rays; a display device; and a controller communicatively coupled to the x-ray source, the x-ray detector, and the display device, the controller configured to: control the x-ray source and the x-ray detector to acquire a plurality of fluoroscopic images of an anatomy of interest in a patient, the plurality of fluoroscopic images depicting an interventional tool positioned relative to the anatomy of interest; segment the interventional tool in the plurality of fluoroscopic images; measure motion of the patient in the plurality of fluoroscopic images; correct the plurality of fluoroscopic images to remove the motion of the patient; register the segmented interventional tool to the anatomy of interest in the corrected plurality of fluoroscopic images; and display, via the display device, images with the segmented interventional tool registered to the anatomy of interest.

In a first example of the system, the controller is further configured to measure the motion of the patient in the plurality of fluoroscopic images by measuring low-frequency motion between a first fluoroscopic image and a second fluoroscopic image of the plurality of fluoroscopic images. In a second example of the system optionally including the first example, the controller is configured to correct the plurality of fluoroscopic images to remove the motion of the patient by subtracting the low-frequency motion from the second fluoroscopic image. In a third example of the system optionally including one or more of the first and second examples, the controller is further configured to register a model of the anatomy of interest to the anatomy of interest in the plurality of fluoroscopic images. In a fourth example of the system optionally including one or more of the first through third examples, the controller is further configured to register the segmented interventional tool to the anatomy of interest in the corrected plurality of fluoroscopic images by registering the segmented interventional tool to the model of the anatomy of interest. In a fifth example of the system optionally including one or more of the first through fourth examples, the controller is further configured to display the images with the segmented interventional tool registered to the anatomy of interest by displaying motion-stabilized views of the segmented interventional tool superimposed on the model of the anatomy of interest.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
acquiring a plurality of fluoroscopic images of an anatomy of interest in a patient, the plurality of fluoroscopic images depicting an interventional tool positioned relative to the anatomy of interest, the plurality of fluoroscopic images including a first fluoroscopic image, a second fluoroscopic image acquired after the first fluoroscopic image, and a third fluoroscopic image acquired after the second fluoroscopic image;
segmenting the interventional tool in the second fluoroscopic image and estimating a position of the interventional tool based on the segmentation of the interventional tool;
measuring motion of the patient in the second fluoroscopic image relative to the first fluoroscopic image;
correcting the estimated position of the interventional tool based on the motion of the patient;
obtaining a previous image of the anatomy of interest of the patient;
registering the segmented interventional tool to the previous image at the corrected estimated position to generate a stabilized image;
displaying the stabilized image alongside the second fluoroscopic image; and
determining that there is no motion of the interventional tool in the third fluoroscopic image relative to the second fluoroscopic image, and in response, displaying the stabilized image alongside the third fluoroscopic image.

2. The method of claim 1, wherein measuring the motion of the patient in the plurality of fluoroscopic images comprises measuring overall motion via optical flow between the first fluoroscopic image and the second fluoroscopic image and decomposing or filtering the overall motion to distinguish the motion of the patient from motion of the interventional tool.

3. The method of claim 2, wherein correcting the estimated positon of the interventional tool based on the motion of the patient comprises subtracting the motion of the patient from the second fluoroscopic image.

4. The method of claim 1, further comprising registering a model of the anatomy of interest to the anatomy of interest in the plurality of fluoroscopic images.

5. The method of claim 4, further comprising retrieving a prior image of the anatomy of interest, and determining the model of the anatomy of interest according to the prior image of the anatomy of interest.

6. The method of claim 5, wherein the prior image comprises a three-dimensional image volume, and wherein the model of the anatomy of interest comprises a projection of a three-dimensional model of the anatomy of interest in a plane of the plurality of fluoroscopic images, the three-dimensional model of the anatomy of interest determined from the three-dimensional image volume.

7. The method of claim 4, wherein registering the segmented interventional tool to the anatomy of interest in the corrected plurality of fluoroscopic images comprises registering the segmented interventional tool to the model of the anatomy of interest.

8. The method of claim 7, wherein displaying the images with the segmented interventional tool registered to the anatomy of interest comprises displaying motion-stabilized views of the segmented interventional tool superimposed on the model of the anatomy of interest.

9. The method of claim 1, wherein the anatomy of interest comprises a tumor or a vessel, wherein the motion of the patient comprises one or more of respiratory motion and cardiac motion, and wherein the previous image comprises a static image of the anatomy of interest acquired prior to acquisition of the plurality of fluoroscopic images.

10. A system, comprising:
an x-ray source configured to generate x-rays;
an x-ray detector configured to detect the x-rays;
a display device; and
a controller communicatively coupled to the x-ray source, the x-ray detector, and the display device, the controller configured to:
control the x-ray source and the x-ray detector to acquire a plurality of fluoroscopic images of an anatomy of interest in a patient, the plurality of fluoroscopic images depicting an interventional tool positioned relative to the anatomy of interest;
segment the interventional tool in the plurality of fluoroscopic images;
measure motion of the patient in the plurality of fluoroscopic images by measuring overall motion via optical flow between at least a first fluoroscopic image and a second fluoroscopic image of the plurality of fluoroscopic images and decomposing or filtering the overall motion to distinguish the motion of the patient from motion of the interventional tool;
estimate motion of the interventional tool with respect to a static anatomy of interest of the patient based on the segmentation of the interventional tool;
register the segmented interventional tool with a previously-acquired image of the patient based on the estimated motion of the interventional tool, the static anatomy of interest present in the previously-acquired image; and
display, via the display device, stabilized interventional tool guidance images with the segmented interventional tool registered to the previously-acquired image of the patient, the stabilized interventional tool guidance images displayed alongside the plurality of fluoroscopic images.

11. The system of claim 10, wherein the controller is further configured to acquire subsequent fluoroscopic images after the plurality of fluoroscopic images, determine that there is no motion of the interventional tool in the subsequent fluoroscopic images, and in response, display a last of the stabilized interventional tool guidance images alongside the subsequent fluoroscopic images.

12. The system of claim 11, wherein the registering only occurs after the motion of the patient is determined and the motion of the interventional tool is estimated, and wherein the motion of the patient is determined and the motion of the interventional tool is estimated only after the interventional tool has been segmented.

13. The system of claim 10, wherein the controller is further configured to register a model of the anatomy of interest to the anatomy of interest in the plurality of fluoroscopic images.

14. The system of claim 13, wherein the controller is further configured to register the segmented interventional tool to the anatomy of interest in the corrected plurality of fluoroscopic images by registering the segmented interventional tool to the model of the anatomy of interest.

15. The system of claim 14, wherein the controller is further configured to display the images with the segmented interventional tool registered to the anatomy of interest by displaying motion-stabilized views of the segmented interventional tool superimposed on the model of the anatomy of interest.

16. A method, comprising:

acquiring a series of fluoroscopic images of an anatomy of interest in a patient, the series of fluoroscopic images depicting an interventional tool positioned relative to the anatomy of interest; and while acquiring the series of fluoroscopic images:

segmenting the interventional tool in the series of fluoroscopic images;

determining motion between a first fluoroscopic image and a second fluoroscopic image of the series of fluoroscopic images;

estimating a position of the interventional tool in the second fluoroscopic image;

decomposing the motion into motion of the patient and motion of the interventional tool;

correcting the estimated position of the interventional tool based on the motion of the patient;

registering the segmented interventional tool to the anatomy of interest at the corrected estimated position; and displaying an image with the registered segmented interventional tool at the corrected estimated position superimposed on the anatomy of interest, the image displayed alongside the second fluoroscopic image.

17. The method of claim 16, further comprising determining a model of the anatomy of interest and registering the model of the anatomy of interest to the anatomy of interest in the corrected second fluoroscopic image.

18. The method of claim 17, wherein registering the segmented interventional tool to the anatomy of interest in the corrected second fluoroscopic image comprises registering the segmented interventional tool to the registered model of the anatomy of interest.

19. The method of claim 18, wherein displaying the image with the registered segmented interventional tool superimposed on the anatomy of interest comprises displaying the image with the registered segmented interventional tool superimposed on the registered model of the anatomy of interest.

20. The method of claim 16, further comprising updating the image of the registered segmented interventional tool superimposed on the anatomy of interest according to motion of the interventional tool in fluoroscopic images acquired subsequent to the second fluoroscopic image, and displaying the updated image; and determining that there is no motion of the interventional tool in a further fluoroscopic image relative to a last of the fluoroscopic image acquired subsequent to the second fluoroscopic image, and in response, displaying the updated image alongside the third fluoroscopic image.

* * * * *